(12) United States Patent
Bruinsma et al.

(10) Patent No.: US 11,026,628 B1
(45) Date of Patent: Jun. 8, 2021

(54) SYSTEMS AND METHODS OF SPATIAL FILTERING FOR MEASURING ELECTRICAL SIGNALS

(71) Applicant: Apple Inc., Cupertino, CA (US)

(72) Inventors: Johannes Anne Bruinsma, Cupertino, CA (US); Erno H. Klaassen, Los Altos, CA (US); Paras Samsukha, San Jose, CA (US); Xiaoyu Guo, San Jose, CA (US)

(73) Assignee: Apple Inc., Cupertino, CA (US)

( * ) Notice: Subject to any disclaimer, the term of this patent is extended or adjusted under 35 U.S.C. 154(b) by 1011 days.

(21) Appl. No.: 15/275,129

(22) Filed: Sep. 23, 2016

Related U.S. Application Data

(60) Provisional application No. 62/235,362, filed on Sep. 30, 2015.

(51) Int. Cl.
*A61B 5/00* (2006.01)
*A61B 5/282* (2021.01)
(Continued)

(52) U.S. Cl.
CPC ............ *A61B 5/681* (2013.01); *A61B 5/0006* (2013.01); *A61B 5/282* (2021.01); *A61B 5/304* (2021.01);
(Continued)

(58) Field of Classification Search
CPC ... A61B 5/0402; A61B 5/0404; A61B 5/0408; A61B 5/04085; A61B 5/0428;
(Continued)

(56) References Cited

U.S. PATENT DOCUMENTS

| 5,483,261 A | 1/1996 | Yasutake |
| 5,488,204 A | 1/1996 | Mead et al. |

(Continued)

FOREIGN PATENT DOCUMENTS

| JP | 2000-163031 A | 6/2000 |
| JP | 2002-342033 A | 11/2002 |
| WO | WO-2014/021886 A1 | 2/2014 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Eun Hwa Kim
(74) *Attorney, Agent, or Firm* — Brownstein Hyatt Farber Schreck, LLP

(57) ABSTRACT

Disclosed herein are devices and methods of using a mobile or wearable device for the acquisition and spatial filtering of ECG signals from an electrode array. One variation of a mobile or wearable device comprises an array of electrodes, one or more reference electrodes, and a controller in communication with the electrodes. In one example, the one or more reference electrodes are located on a wrist-worn device (e.g., a watch), and the electrode array is located on an accessory device that may be contacted with a fingertip. One variation of a spatial filtering method comprises identifying the electrodes that have high levels of noise and excluding the ECG signals from those electrodes from further analyses. In another variation, a method of spatial filtering comprises identifying electrodes with low levels of noise and including only the ECG signals from those electrodes in further analyses.

19 Claims, 8 Drawing Sheets

(51) Int. Cl.
*A61B 5/304* (2021.01)
*A61B 5/316* (2021.01)
*A61B 5/332* (2021.01)

(52) U.S. Cl.
CPC .............. *A61B 5/316* (2021.01); *A61B 5/332* (2021.01); *A61B 5/7214* (2013.01); *A61B 2560/0468* (2013.01); *A61B 2562/0209* (2013.01)

(58) Field of Classification Search
CPC ..... A61B 5/681; A61B 5/6824; A61B 5/6825; A61B 5/6826; A61B 5/6887; A61B 5/6897; A61B 5/6898; A61B 5/72; A61B 5/7203; A61B 5/7221; A61B 5/7225
See application file for complete search history.

(56) References Cited

U.S. PATENT DOCUMENTS

| | | | |
|---|---|---|---|
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,197,351 B2 | 3/2007 | Umeda et al. | |
| 7,616,110 B2 | 11/2009 | Crump et al. | |
| 7,663,607 B2 | 2/2010 | Hotelling et al. | |
| 8,301,232 B2 | 10/2012 | Albert et al. | |
| 8,378,811 B2 | 2/2013 | Crump et al. | |
| 8,479,122 B2 | 7/2013 | Hotelling et al. | |
| 8,618,930 B2 | 12/2013 | Papadopoulos et al. | |
| 9,351,653 B1* | 5/2016 | Harrison | A61B 5/04014 |
| 2006/0167368 A1* | 7/2006 | Sarkela | A61B 5/04014 |
| | | | 600/544 |
| 2006/0197753 A1 | 9/2006 | Hotelling | |
| 2013/0150697 A1* | 6/2013 | Imai | A61B 5/296 |
| | | | 600/384 |
| 2013/0274583 A1* | 10/2013 | Heck | A61B 5/6803 |
| | | | 600/383 |
| 2013/0338519 A1* | 12/2013 | Chen | A61B 5/0452 |
| | | | 600/521 |
| 2014/0107457 A1* | 4/2014 | Raghunathan | A61B 5/0006 |
| | | | 600/386 |
| 2014/0155705 A1 | 6/2014 | Papadopoulos et al. | |
| 2015/0018660 A1* | 1/2015 | Thomson | A61B 5/0404 |
| | | | 600/393 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

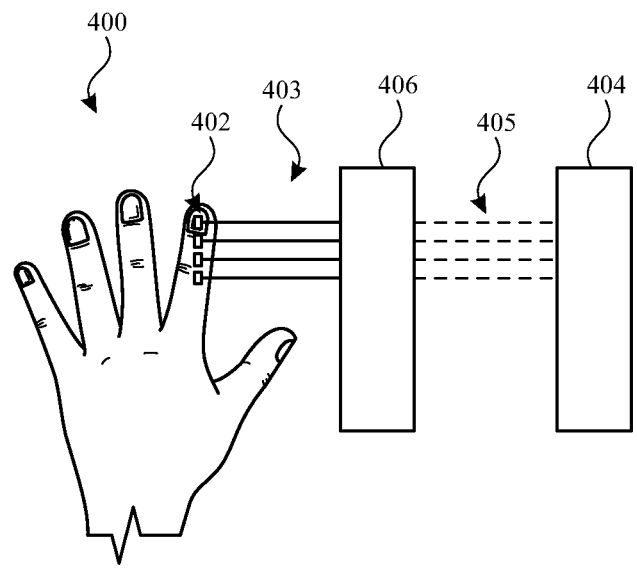
FIG. 4A
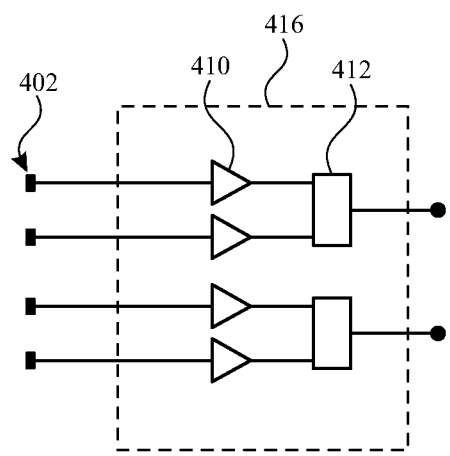 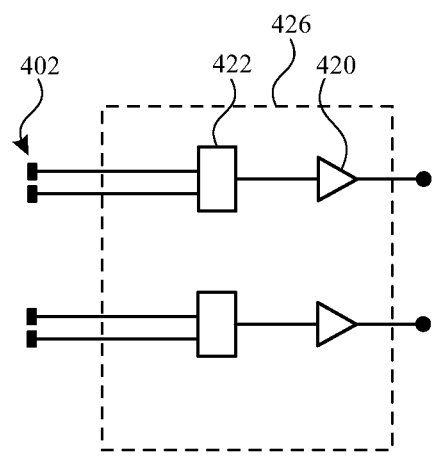
FIG. 4B          FIG. 4C

SYSTEMS AND METHODS OF SPATIAL FILTERING FOR MEASURING ELECTRICAL SIGNALS

CROSS-REFERENCE TO RELATED APPLICATIONS

This application claims priority to U.S. Provisional Patent Application Ser. No. 62/235,362 filed Sep. 30, 2015, which is hereby incorporated by reference in its entirety for all purposes.

FIELD

This relates generally to systems including a plurality of measurement electrodes and methods for measuring one or more electrical signals using the plurality of measurement electrodes.

BACKGROUND

Electrocardiogram (ECG) waveforms can be generated based on the electrical activity of the heart during each heartbeat. The waveforms can be recorded from multiple electrical leads attached to various areas of a patient's chest and limbs. FIG. 1 depicts one example of a 12-lead ECG system 100 with a group of six measurement electrodes 102A, 102B, 102C, 102D, 102E, and 102F that can be placed across the patient's chest, and four measurement electrodes 103A, 103B, 103C, and 103D that can be attached to the patient's limbs. The measurement electrodes for ECG data acquisition can include a conducting or electrolytic gel (e.g., Ag/AgCl gel) to provide a continuous, electrically-conductive path between the skin and the electrodes. Such "wet" electrodes can reduce the impedance at the electrode-skin interface, thereby facilitating the acquisition of a low-noise ECG signal. All of the measurement electrodes 102A, 102B, 102C, 102D, 102E, 102F, 103A, 103C, and 103D can be connected to a control module 104, where signals from the measurement electrodes can be transmitted to control module 104 for storage, processing, and/or displaying.

The signals from the ten measurement electrodes can be summed together to generate a single ECG waveform that can be viewed by the patient and/or a medical practitioner to evaluate the electrical activity of the heart. In some instances, the ECG signals from some of the measurement electrodes can have larger fluctuations than the other measurement electrodes. These larger fluctuations can be caused by noise due to, for example, poor skin contact, other electronic devices and/or sources of electromagnetic radiation, and/or user motion artifacts. Since the signals from the ten measurement electrodes can be summed together, discerning which among the ten measurement electrodes is associated with unsuitable levels of noise may be difficult. Reducing and/or compensating for the effect of these noise sources may be desirable to yield an overall ECG waveform that has reduced noise levels and facilitates interpretation by the patient and/or medical practitioner.

BRIEF SUMMARY

Disclosed herein are devices and methods of using a mobile or wearable device for the acquisition and spatial filtering of ECG signals from an electrode array. The mobile or wearable device can comprise a plurality of measurement electrodes, one or more reference electrodes, and a controller in communication with the electrodes. In some examples, the electrodes can be dry electrodes. In some variations, the one or more reference electrodes may be located on a wrist-worn device, such as a bracelet, wrist band, or watch, such that the reference electrodes can contact the skin in the wrist region, while the plurality of measurement electrodes can be configured to contact a second, different skin region. In some examples, the plurality of measurements electrodes can be located on a separate component from the reference electrode(s). In some examples, some or all of the plurality of measurement electrodes can be located on a wrist or finger cuff, a fingertip cover, a second wrist-worn device, a region of the wrist-worn device that can be different from the location of the reference electrode(s), and the like. One or more electrical signals measured by the plurality of measurement electrodes can be spatially filtered by the controller such each signal can be capable of being individually rejected if the signal has more noise relative to the signals from other measurement electrodes. For example, the controller of the mobile or wearable device can employ various methods to determine which measurement electrode(s) have noise levels that exceed a predetermined and/or computed noise threshold and can exclude the input from those measurement electrode(s) in the computation of the ECG waveform. The noise threshold may, for example, be the average noise level from all of the plurality of measurement electrodes as computed by the controller. In some examples, signals from the measurement electrode(s) with suprathreshold levels (i.e., signal levels greater than a second predetermined threshold) of noise can be incorporated into the ECG waveform, but can be given less weight less than signals from measurement electrode(s) with subthreshold levels of noise (i.e., signal levels less than a first predetermined threshold, where the first predetermined threshold can be less than the second predetermined threshold).

In some examples, the plurality of measurement electrodes can be connected to the controller via an interface module. The interface module can include one or more multiplexers having a plurality of selectable channels connected to each of the plurality of measurement electrodes. In some examples, each measurement electrode can have a dedicated channel in the multiplexer; in other examples, the measurement electrodes can share a channel with one or more other measurement electrodes such that the multiplexer can selectively connect the measurement electrodes to the controller based on commands from the controller. The connections between the measurement electrodes and the interface module can be wired or wireless, and/or the connections between the interface module and the controller may be wired or wireless. Examples of wireless communication protocols can include Wi-Fi, Bluetooth, near field communication (NFC), cellular, and/or other wireless communication techniques. The controller can issue commands to the interface module such that connections to measurement electrodes with subthreshold levels of noise (i.e., "low-noise" measurement electrodes) can be preferred or prioritized over the connections to measurement electrodes with suprathreshold levels of noise (i.e., "high-noise" measurement electrodes). For example, low-noise measurement electrodes can be sampled more frequently than high-noise measurement electrodes, and in some variations, high-noise measurement electrodes may not be sampled at all. In instances where multiple measurement electrodes can share a single channel on a multiplexer of the interface module, fewer wires (e.g., leads) may be used and the size of the wearable or mobile device upon which some or all of the measurement electrodes is mounted can be smaller. Regulating the multiplexer connections such that low-noise measurement electrodes are favored over high-noise measurement electrodes can allow for this reduction in hardware size and complexity with little or no impact on the sampling of low-noise measurement electrodes.

Also described herein are methods of spatially filtering signals. Spatial filtering methods can comprise identifying measurement electrodes with subthreshold levels of noise (e.g. by comparing the noise from each measurement electrode with a noise threshold), optionally identifying measurement electrodes with suprathreshold levels of noise, and analyzing the signals from the measurement electrodes with subthreshold levels of noise. For example, some methods may comprise generating an overall ECG waveform and/or computing the user's heart rate based primarily on ECG data from measurement electrodes with subthreshold levels of noise. In some examples, spatial filtering can comprise eliminating or not acquiring ECG data from measurement electrodes with suprathreshold levels of noise (e.g., only acquiring ECG data from measurement electrodes with subthreshold levels of noise). In some examples, spatial filtering can comprise adjusting the sampling rate or frequency of high-noise measurement electrodes to be less than the sampling rate or frequency of low-noise measurement electrodes. Optionally, the controller can increase the sampling frequency on the measurement electrodes with subthreshold noise levels. Alternatively or additionally, spatial filtering methods may comprise scaling down the contribution of the high-noise measurement electrodes when computing the overall ECG waveform and/or computing the user's heart rate. In some examples, the measurement electrodes that have the least amount of noise can have a dedicated channel through the interface module so that the controller can receive measurements from that measurement electrode at the highest sampling frequency, while the measurement electrodes that have suprathreshold noise levels may share a channel with other measurement electrodes having relatively high levels of noise, such that the effective sampling frequency of these high-noise electrodes can be reduced. In doing so, for a given data acquisition interval, the controller can acquire more data from low-noise measurement electrodes and less data from the high-noise measurement electrodes. In some variations, the ECG waveform can be more heavily weighted towards ECG data measured by the low-noise measurement electrodes, while still representing ECG data (albeit at a lower weight or degree) from the high-noise measurement electrodes.

Described herein is an exemplary wearable electrocardiographic (ECG) device that can comprise a plurality of dry measurement electrodes, which can be measurement electrodes configured to contact a skin surface and capable of obtaining an accurate signal without the use of a conducting or electrolytic gel. The plurality of dry measurement electrodes can be in communication with a controller, which can be configured to receive signals from the plurality of measurement electrodes at a first sampling frequency. In some examples, the controller can be configured to generate an ECG waveform using the average of the signals from the plurality of measurement electrodes that do not exceed the noise threshold. The ECG waveform may be, for example, a weighted sum of the signals from the plurality of measurement electrodes, where the weighting factor for the each signal can be inversely proportional to the noise level of that measurement electrode. For example, the weighting factor for signals from measurement electrodes with suprathreshold noise levels may be zero. The weighting factor can vary as a function of time in some examples. Optionally, the wearable ECG device can comprise a display in communication with the controller, where the controller can be configured to output the ECG waveform to the display for viewing. In some examples, the controller can be configured to transmit the ECG signals to a companion device. The companion device can comprise a controller that can be configured to combine the signals from measurement electrodes that have noise levels that do not exceed the noise threshold to generate an ECG waveform. The companion device controller can be configured to generate an ECG waveform by averaging the ECG signals from measurement electrodes that have noise levels that do not exceed the noise threshold. In some variations, the controller can be configured to compute one or more physiological parameters (e.g., a heart rate) of the user based on the ECG waveform.

In some variations, the array of dry electrodes may be located on a wrist-worn device, and/or may be configured to communicate wirelessly to the controller. The noise threshold may be predetermined or computed. For example, the noise threshold may be derived from the average noise level of all of the signals, and the controller may be configured to compare the noise levels from each of the measurement electrodes with this computed noise threshold to identify the measurement electrodes that have suprathreshold noise levels. The controller may be configured to compare the noise levels of the measurement electrodes at a selected frequency, where the selected frequency may be the sampling frequency. The controller may be configured to identify and reject the data from any measurement electrode that has a noise level that can be more than one standard deviation from the noise threshold. For example, the controller may be configured to identify and reject the data from any measurement electrode that has a noise level that can be more than two standard deviations from the noise threshold. The controller may be configured to sample each measurement electrode at a selected sampling frequency, wherein the sampling frequency can be inversely related to the noise level of that measurement electrode. In some examples, the sampling frequency for a measurement electrode with noise levels greater than two standard deviations from the noise threshold can be zero.

Some examples can include an ECG device further comprising an interface module including a multiplexer in communication with the plurality of measurement electrodes and the controller. The multiplexer may be configured to dynamically connect the controller to electrodes that have threshold or subthreshold levels of noise. In some examples, the multiplexer may be configured to provide a connection between the controller and the measurement electrode(s) that have threshold or subthreshold noise levels such that these measurement electrodes can be sampled by the controller at a second sampling frequency (e.g., the second sampling frequency may be the same as the first sampling frequency). The multiplexer may, in some variations, be configured to provide a connection between the controller and the measurement electrode(s) that have suprathreshold noise levels such that these measurement electrodes can be sampled by the controller at a third sampling frequency, which can be less than the second sampling frequency.

Also described herein are methods of spatial filtering. For example, a method for spatial filtering across a plurality of measurement electrodes can comprise contacting a reference electrode to a first skin region on a user, contacting one or more of the plurality of measurement electrodes to a second skin region on the user, where the reference electrode and the plurality of measurement electrodes can be in communication with a controller, measuring noise levels for each measurement electrode, computing a noise threshold based on an average noise level across all of the measurement electrodes, and acquiring signals from the measurement electrodes that have noise levels at or below the noise threshold. In some examples, the method may further comprise averaging the acquired signals, using the controller, to generate an ECG waveform. Optionally, some methods may further comprise acquiring signals from the measurement electrode(s) that have noise levels above the average noise level. The signals from high-noise measurement electrodes with suprathreshold noise levels may be acquired at a lower sampling frequency than the signals from measurement electrodes with threshold or subthreshold noise levels. Measuring noise levels may comprise measuring the impedance of each measurement electrode. In some examples, the method may also comprise comparing the average noise level to a predetermined noise threshold, and if the controller determines that the average noise level exceeds the threshold, generating a notification to the user to position one or more of the plurality of measurement electrodes at a different skin location and/or apply pressure to the measurement electrode(s). Optionally, the method may further comprise displaying the ECG waveform to the user. In some variations, the communication between the plurality of measurement electrodes and controller may be modulated by a multiplexer. The multiplexer may connect the controller more frequently to measurement electrodes that have threshold or subthreshold noise levels and less frequently to measurement electrodes that have suprathreshold noise levels.

BRIEF DESCRIPTION OF THE DRAWINGS

FIG. 4A is a schematic of one variation of a system for the acquisition and spatial filtering of signals.

FIG. 4B depicts a circuit schematic that represents one variation of an interface module.

FIG. 4C depicts a circuit schematic that represents another variation of an interface module.

DETAILED DESCRIPTION

Figure 1:
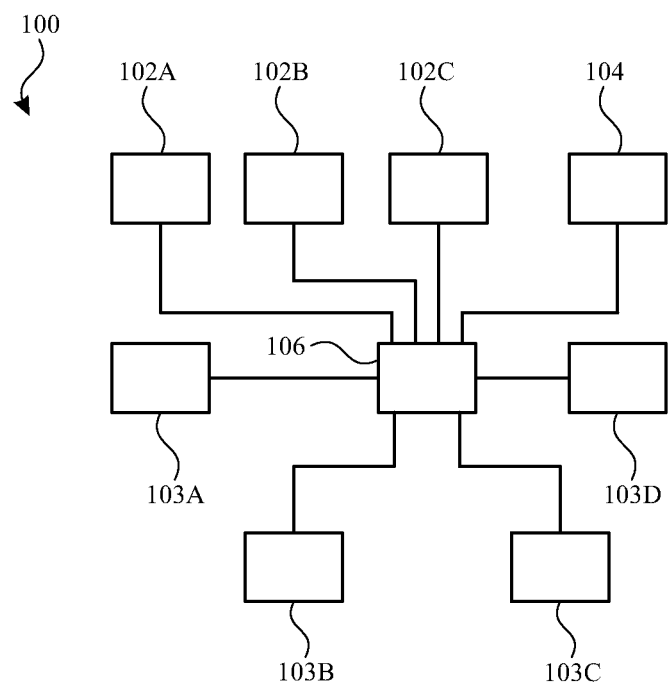
FIG. 1 schematic depiction of a traditional ECG system.

Disclosed herein are devices and methods of using a mobile or wearable device for the acquisition and spatial filtering of signals from a plurality of measurement electrodes. The mobile or wearable device may comprise a plurality of measurement electrodes, one or more reference electrodes, and a controller in communication with the measurement and/or reference electrodes. In some examples, the measurement electrodes can be dry electrodes. In some examples, the mobile or wearable device may comprise an interface module in communication with the measurement electrodes and the controller, where the interface module can be configured to adjust the connectivity between the plurality of measurement electrodes and the controller. In some examples, the interface module may comprise one or more multiplexers configured for the selection of individual and/or sets of measurement electrodes based on command signals from the controller. Methods of spatial filtering the signals from the measurement electrodes may comprise using the interface module to selectively transmit data from low-noise measurement electrode(s). Data from the measurement electrode(s) that have been determined to have high levels of noise (e.g., noise levels that exceed a predetermined and/or computed noise threshold) may be filtered out and may not be included in the generation of the overall ECG waveform. In some examples, filtering out data from high-noise measurement electrodes may comprise adjusting the connectivity of the multiplexer (s) of the interface module such that data from these high-noise measurement electrodes may not transmitted to the controller. Alternatively or additionally, filtering out data from high-noise measurement electrodes may comprise adjusting the connectivity of the multiplexer such that the frequency or rate at which the multiplexer connects the controller to the high-noise measurement electrodes can be lower than the frequency or rate at which the multiplexer(s) connect the controller to the low-noise measurement electrodes. In examples where each of the measurement electrodes has a dedicated channel to the controller, spatial filtering the signals across the plurality of measurement electrodes may comprise the controller rejecting, ignoring, and/or eliminating the data from the high-noise measurement electrodes from data analysis and interpretation. For example, the controller may incorporate only the signals from low-noise measurement electrodes in the computation of the overall ECG waveform. In some variations, the controller may generate an overall ECG waveform by computing a weighted sum across all of the measurement electrode signals. Spatial filtering of the signals from the plurality of measurement electrodes may comprise assigning a weight to a particular measurement electrode signal that can be inversely related (e.g., inversely proportional, etc.) to its ranked noise level as compared to the other measurement electrodes and/or the average noise level across all of the electrodes. In this variation, the signal(s) from high-noise measurement electrode(s) may be incorporated in the overall ECG waveform, but at a relatively lower weight as compared to the signal(s) from low-noise measurement electrode (s). Reducing the contribution of high-noise measurement electrode(s) may also reduce their impact to the signal-to-noise ratio (SNR) of the overall ECG waveform.

Although the examples and applications of spatial filtering devices and methods are described in the context of generating a complete ECG waveform, it should be understood that the same or similar devices and methods may be used to collect and process data from the plurality of measurement electrodes and may or may not generate an ECG waveform. For example, the spatial filtering of the signals from the plurality of measurement electrodes may facilitate the monitoring of certain cardiac characteristics (e.g., heart rate, arrhythmias, changes due to medications or surgery, function of pacemakers, heart size, etc.) and/or ECG waveform characteristics (e.g., timing of certain waves, intervals, complexes of the ECG waveform) by the controller and/or user without generating a complete ECG waveform. In some examples, the controller may generate a subset of the ECG waveform (e.g., one or more of the P wave, QRS complex, PR interval, T wave, U wave) based on spatially filtered measurement electrode signals. The ECG devices described herein may optionally comprise a display that can provide a visual representation of the collected and/or filtered measurement electrode data to the user. Alternatively or additionally, the filtered measurement electrode data may not be displayed by the ECG device, but instead can be relayed to a companion device (e.g., a tablet, laptop, smartphone, computer, server, etc.) that can have a display for outputting a visual representation of the data. Moreover, examples of the disclosure include spatial filtering devices and methods configured for other types of measurements including, but not limited to, EEG and EMG measurements or optical determination of parameters on blood constituents.

The terminology used in the description of the variations described herein is for the purpose of describing particular variations only and is not intended to be limiting. As used in the description of the various described variations and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Variations of electronic devices, user interfaces for such devices, and associated processes for using such devices are described. In some variations, the device can be a portable communications device, such as an internet-enabled telephone such as a smartphone, a mobile telephone, or a wearable communications device, such as a wristband, watch, clip, headband, earphone or ear piece, internet-enabled eyewear, or any computing device, portable or otherwise, such as a personal calendaring device, electronic reader, tablet, desktop, or laptop computers, etc. Any of these devices may also include other functions, such as personal digital assistant (PDA) and/or music player functions. Optionally, any of the above-listed electronic devices may comprise touch-sensitive surfaces (e.g., touch screen displays and/or touchpads). Alternatively or additionally, the electronic devices may include one or more other physical user-interface devices, such as a physical mouse, a keyboard, and/or a joystick.

Figure 2A:
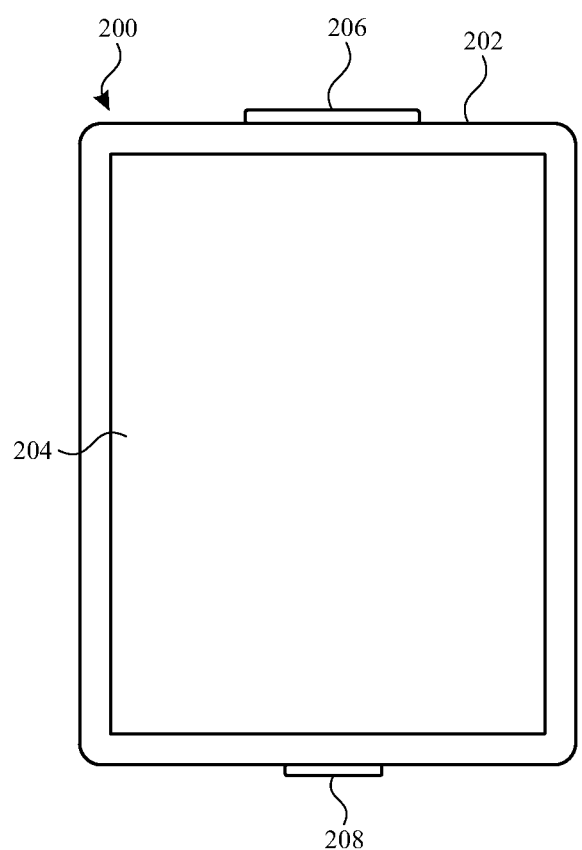
FIG. 2A illustrates a personal electronic device in accordance with some examples.

FIG. 2A illustrates exemplary personal electronic device 200, such as one that may be used for acquiring and spatially filtering signals from electrode arrays for generating ECG waveforms. Device 200 includes body 202. Personal electronic device 200 may be a portable device such as a tablet, smart phone, watch, and in some variations, may be part of a wireless-capable eyepiece or eye-wear, head gear, and the like. In other variations, personal electronic device 200 may not be a portable device, and may be desktop computer. In some variations, device 200 has touch-sensitive display screen 204. Alternatively, or in addition to touch screen 204, device 200 may have a display and a touch-sensitive surface. In some variations, touch screen 204 (or the touch-sensitive surface) may have one or more intensity (force) sensors for detecting intensity of contacts (e.g., touches) being applied. The one or more intensity sensors of touch screen 204 may provide output data that represents the intensity of touches. The user interface of device 200 can respond to touches based on their intensity. For example, touches of different intensities can invoke different user interface operations on device 200.

Figure 2B:
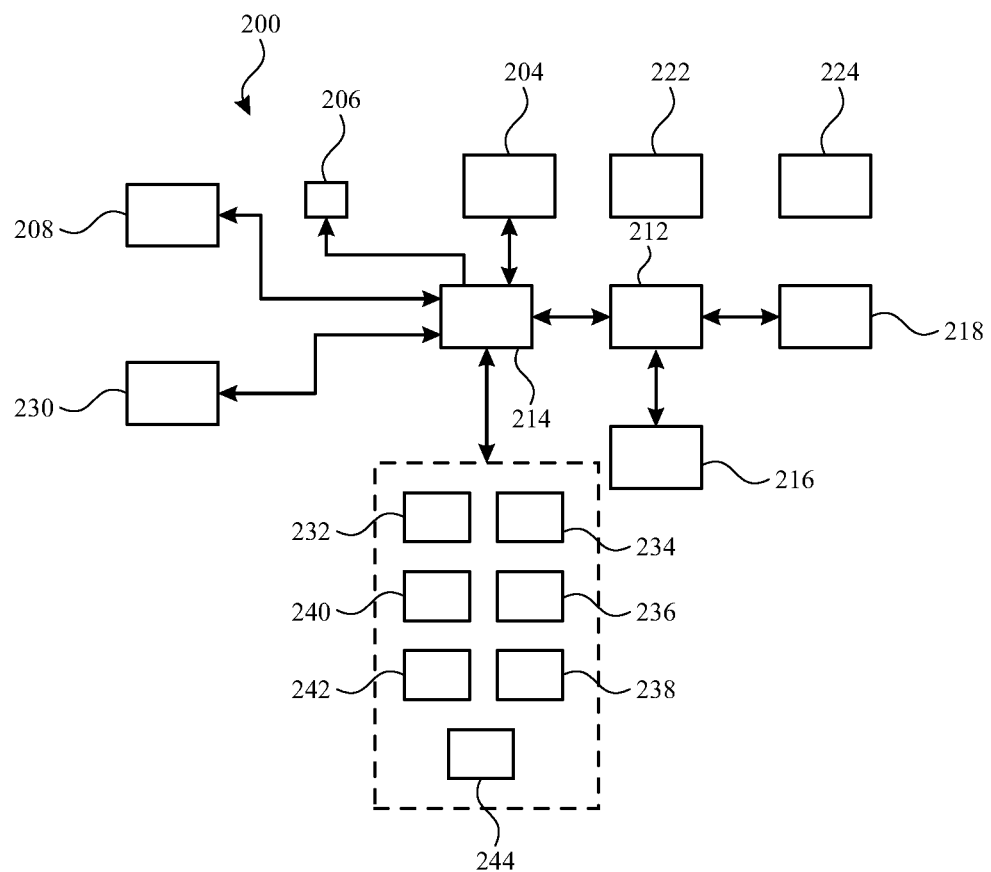
FIG. 2B is a block diagram illustrating a personal electronic device in accordance with some examples.

FIG. 2B depicts the various components of exemplary personal electronic device 200. Similar components may also be included in any of the devices described herein (e.g., device 300, 310 of FIGS. 3A-3C). Device 200 can include a bus 212 that operatively couples I/O section 214 with one or more computer processors 216 and memory 218. I/O section 214 may be connected to display 204, which may have a touch-sensitive component 222 and, optionally, a touch-intensity sensitive component 224. In addition, I/O section 214 may be connected with communication unit 230 for receiving application and operating system data, using Bluetooth, Wi-Fi, near field communication (NFC), cellular, and/or other wireless communication techniques. Device 200 may include input mechanisms 206 and/or 208. Input mechanism 206 may be a rotatable input device or a depressible and rotatable input device, for example. In some examples, input mechanism 208 may be a button.

Input mechanism 208 may be a microphone, in some examples. Personal electronic device 200 can include various sensors, such as GPS sensor 232, accelerometer 234, directional sensor 240 (e.g., compass), gyroscope 236, motion sensor 238, and/or a combination thereof, all of which can be operatively connected to I/O section 214. Examples with ECG measurement capabilities, described in greater detail below, may include one or more reference electrodes 242 and an array of measurement electrodes 244. The connection between the various sensors and the I/O section 214 may be an electrical wire or bus, and/or wireless (e.g., Bluetooth, Wi-Fi, near field communication (NFC), cellular, and/or other wireless communication techniques).

Memory 218 of personal electronic device 200 can be a non-transitory computer-readable storage medium, for storing computer-executable instructions, which, when executed by one or more computer processors 216, for example, can cause the computer processors to perform the techniques and methods described herein. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. A "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. Examples of such storage include magnetic disks, optical discs based on DVD, CD, or Blu-ray technologies, as well as persistent solid-state memory such as flash, solid-state drives, and the like. Personal electronic device 200 may not be limited to the components and configuration of FIG. 2B, but can include other or additional components in multiple configurations. As described herein, a "controller" may refer to a system comprising a computer processor such as a microprocessor, central processing unit (CPU), a digital signal processor (DSP), programmable logic device (PLD), and/or the like.

In some variations, device 200 may have one or more input mechanisms 206 and 208. Input mechanisms 206 and 208, if included, can be physical. Examples of physical input mechanisms may include rotatable mechanisms and push buttons. In some variations, device 200 may have one or more attachment mechanisms. Such attachment mechanisms, if included, can permit attachment of device 200 with, for example, hats, eyewear, earrings, necklaces, shirts, jackets, pockets, collars, bracelets, watch straps, chains, trousers, belts, shoes, socks, purses, backpacks, undergarments, and so forth. These attachment mechanisms may permit device 200 to be worn by a user.

Attention is now turned toward variations of additional device modules and associated processes that may be implemented on an electronic device, such as portable multifunction device 300, for acquiring ECG signals from an electrode array and spatial filtering of those signals.

Figure 3A:
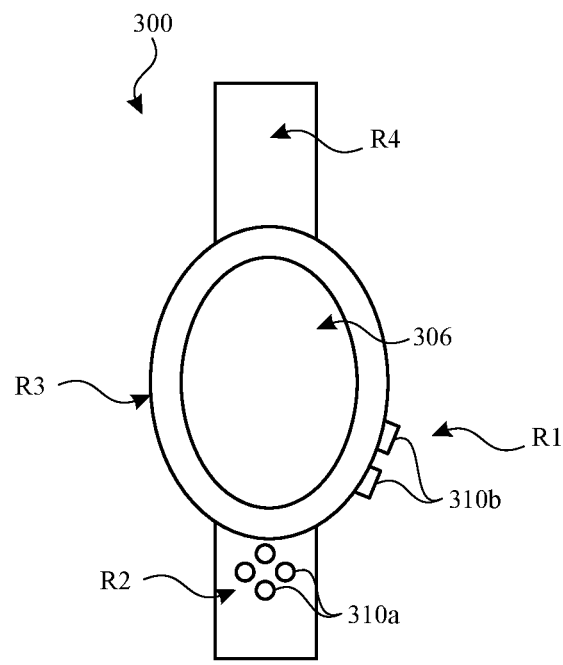
FIG. 3A is a perspective view of one variation of a watch that may be used for the acquisition and processing of signals from the measurement and/or reference electrodes.
Figure 3B:
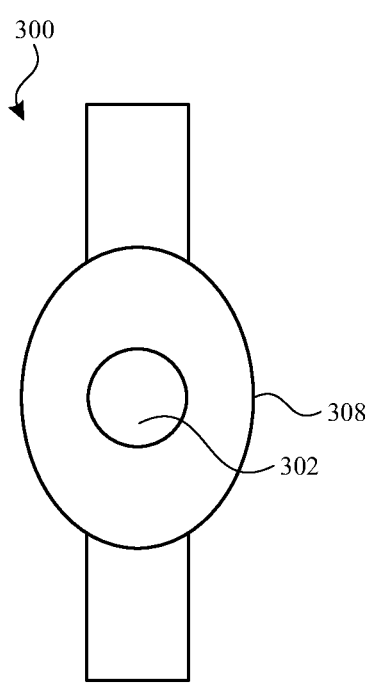
FIG. 3B is view of the back of the watch of FIG. 3A.
Figure 3C:
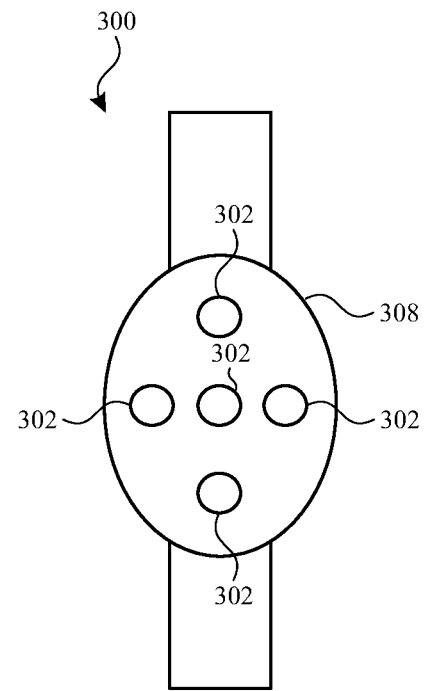
FIG. 3C is another variation of the back of the watch of FIG. 3A.

FIGS. 3A-3C depict one variation of a mobile or wearable device 300 that may be used to acquire and spatially filter signals from a plurality of measurement electrodes. The device 300 may be a wrist-worn device, such as a watch, bracelet, or wrist band. The device 300 may comprise one or more reference electrodes 302 located on a skin-contacting surface of the device. For example, the device may be a watch having a housing with a front side 306 that can face the user and a back side 308 that can contact the skin region around the wrist. As depicted in FIG. 3B, a reference electrode 302 can be located on the back side 308. In this example, only one reference electrode 302 is depicted, however, in other variations, such as depicted in FIG. 3C, there may be more than one reference electrode (e.g., 2, 3, 4, 5, 6, 7, 8, 9, 10, 12, 14, 15 or more, etc.).

In some examples, a plurality of measurement electrodes 310 may be located on the device 300 (e.g., on the back side 308 and/or front side 306), as illustrated in FIG. 3A. In some examples, the plurality of measurement electrodes can be located on an accessory that can be separate or detached or detachable from the device 300. One or more of the plurality of measurement electrodes can be provided at various locations or regions of the device 300. For example, plurality of measurement electrodes 310 can be located at a first side wall portion R1 of the device 300 and/or a second side wall portion R3 of the device. Alternatively or additionally, one or more measurement electrodes can be located on the outward-facing surface of the wrist band of the device 300. For example, one or more measurement electrodes can be on the outward-facing surface of the band R2 located below the housing or can be on the outward-facing surface of the band located above the housing R4. Some examples may include a first one or more measurement electrodes located at R1 and a second one or more measurement electrodes located at R2. The user's ECG data can be collected when the user puts his/her thumb on the first one or more measurement electrodes and his/her index finger on the second one or more measurement electrodes. In some examples, there may only be one location included measurement electrodes on the device 300. The signals measured by the one or more measurement electrodes can be transmitted to the device 300 using wireless communications or using one or more electrical wires or cables.

The electrodes of the electrode arrays described herein may be "dry" electrodes. "Dry electrodes" can be electrodes configured to contact the user without use of a conducting or electrolytic gel located between the user's skin and any surface of the electrodes. Typically, ECG measurement systems use wet Ag/AgCL electrodes. Without the aid of such gels, obtaining electrical signals with an acceptable or favorable SNR can be challenging. Low-frequency noise (e.g., about 0.5 Hz to about 40 Hz) may be introduced at the electrode-skin interface. This frequency band also encompasses the ECG signals-of-interest, which may pose a challenge (e.g., make it computationally intensive) to filtering out the noise without diminishing the signal strength and/or integrity. Without wishing to be bound by theory, sources of such low-frequency noise may include sweat glands (e.g., due to electrolyte behavior), local motion artifacts, local dead skin and other skin irregularities, as well as non-homogenous skin contact. Furthermore, measuring ECG signals from different sites on the limbs (e.g., hand(s), finger(s), feet, toe(s)) may introduce noise of a highly stochastic nature. Such stochastic noise may have a peak-peak value great than about 50 µVpp, which can exceed the noise threshold that can be acceptable for ECG measurements and waveforms. In some cases, these noise sources may be localized and spatially specific. That is, if an electrode array is placed on a small patch of skin (e.g., about 1 $cm^2$, about 2 $cm^2$, etc.), the measurements from one electrode in the electrode array can be affected by noise from sweat glands, while another electrode in the electrode array may not be affected by sweat glands. In this example, the distribution of noise across the electrode array can depend on the distribution of sweat glands across that patch of skin.

Figure 3D:
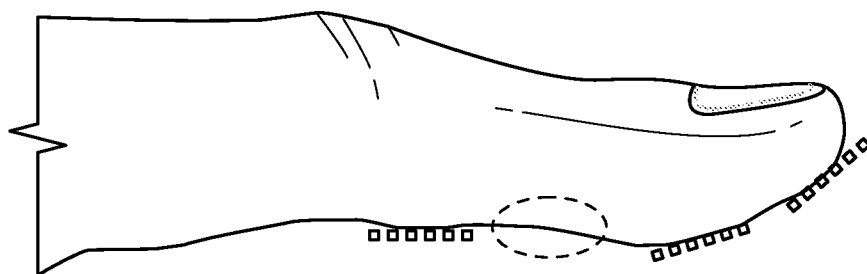
FIG. 3D depicts the skin contours of a finger.

In some instances, the electrode array can make poor or inconsistent contact with the user's skin. This may be particularly the case when ECG data is being collected from anatomical structures with irregular curves and shapes, such as from a fingertip. FIG. 3D schematically depicts a finger, which may have a constantly-changing surface (denoted by the constantly-changing slopes of the dotted lines), as well as concave or convex regions (a concave region is enclosed in the dotted oval). Other geometric surface irregularities may also include curves that have non-constant radius of curvature, skin folds or clefts, variable surface elasticity of different types of tissue (e.g., finger nails, bones, are relatively inelastic as compared to skin), etc. These irregularities may increase the impedance of an electrode and render the ECG signals acquired by that electrode particularly susceptible to noise (especially from motion artifacts).

The devices and methods disclosed herein address these and other sources of noise by utilizing a plurality of individually-controllable/measurable measurement electrodes and spatial filtering of the signals acquired by the plurality of measurement electrodes. Spatial filtering of the signals acquired by the plurality of measurement electrodes may comprise measuring the noise levels for each of the measurement electrodes, determining which measurement electrode(s) have noise levels that are at, above, or below a noise threshold, and excluding the data from high-noise measurement electrode(s) in the computation of the overall ECG waveform. Filtering out the signals from the high-noise measurement electrode(s) may improve the quality of the overall ECG waveform and/or simplify the computational processing of the ECG data acquired by the measurement electrodes.

FIG. 4A depicts a schematic functional block diagram of an exemplary system for measuring ECG signals from a plurality of individually-controllable/measurable measurement electrodes and spatial filtering those signals. The system 400 may comprise plurality of measurement electrodes 402, a controller 404, and an interface module 406. Interface module 405 can be configured to transmit signals from the plurality of measurable electrodes 402 to the controller 404. One or more reference electrodes may be in communication with the interface module and/or controller. The communication channel 403 (between the plurality of measurement electrodes 402 and the interface module 406) and the communication channel 405 (between the interface module 406 and the controller 404) may be wired or wireless. The communication channels may transmit signals that can represent measured ECG data or signals, controller commands to the interface module, and the like. In some examples, the signal transmitted to the controller can be a differential signal (e.g., a signal representing the difference between signal values measured at two or more measurement electrodes). As described previously with regard to FIGS. 3A-3C, the plurality of measurement electrodes 402, interface module 406, and the controller 404 may be located on the same device or may be located on separate devices or components. For example, the plurality of measurement electrodes 402, interface module 406, and the controller 404 may all be located on a wrist-worn device such as a watch. Alternatively, the interface module 406 and the controller 404 may be located on the wrist-worn device while the plurality of measurement electrodes 402 may be located on a separate accessory device. In some examples, the communication channel 403 may be wireless, while the communication channel 405 may be wired. In some examples, the electrode array 402 and the interface module 406 may be located on an accessory device, and the controller may be located on a wrist-worn device. In some examples, the communication channel 403 may be wired, while the communication channel 405 may be wireless. Although the plurality of measurement electrodes 402 is depicted as having four electrodes in FIG. 4A, it should be understood that the plurality of measurement electrodes may comprise any number of electrodes, as may be desirable. For example, the plurality of measurement electrodes 402 may comprise 2, 3, 4, 5, 6, 7, 8, 9, 10, 11, 12, 15, 20, 22, 24, 25, 27, 30, etc. electrodes. The arrangement of these measurement electrodes may vary, for example, depending on the size and size of the anatomical region from which the plurality of measurement electrodes can be used to measure ECG signals. For example, the plurality of measurement electrodes may be arranged as a circle, rectangle, diamond, triangle, in a line, or in any anatomically-specific fashion, etc.

The interface module 406 can be configured to amplify and filter the signals from the electrodes. In some examples, the interface module 406 can selectively transmit the signals measured by the plurality of measurement electrodes to the controller. For example, the interface module 406 may comprise one or more buffers, filters (e.g., 60 Hz notch filters, bandpass filters, etc.), amplifiers (e.g., differential amplifiers, etc.), and/or analog-to-digital converter (ADC). In some examples, the raw signals measured by the plurality of measurement electrodes may be filtered, amplified, and converted to a digital signal before the signals are transmitted from the interface module to the controller. Optionally, in some variations, the interface module 406 may comprise a switch circuit, such as a multiplexer, where ECG signals from each of the measurement electrodes can be transmitted to the multiplexer (either before or after amplifying, filtering and/or converting to a digital signal). Based on commands from the controller, the multiplexer can selectively output or transmit the data from certain measurement electrodes to the controller. The number of multiplexer output channels may be the same as or less than the number of measurement electrodes. Multiplexing the data collected by the plurality of measurement electrodes may help to reduce the number of signal processing components in the interface module, thereby reducing the size of the overall device. In some examples, the interface module may comprise a plurality of multiplexers, for example, arranged serially or in stages. Furthermore, the multiplexer may be used to selectively transmit the signals from the relatively low-noise measurement electrodes to the controller instead of the signals from the relatively high-noise measurement electrodes. By doing so, the multiplexer can spatially filter the signals from the measurement electrodes based on commands from the controller by rejecting the high-noise signals and transmitting the low-noise signals.

FIGS. 4B-4C depict examples of interface modules 416, 426 that comprise a plurality of amplifiers and multiplexers. FIG. 4B depicts an interface module 416 that comprises amplifiers 410 and multiplexers 412, such that the signals from each measurement electrode 402 can be amplified before they arrive at the input ports of the multiplexers. In some examples, interface module 416 can include circuitry configured to reject any signals from measurement electrodes 402 that may be associated with high noise (i.e., the noise is greater than a noise threshold). In this manner, only low-noise signals can be transmitted through communication channel 405 to controller 404. In some examples, the high-noise signals may be rejected (e.g., not sent through communications channel 405 to controller 404) for a certain time period, followed by a periodic check/determination whether the electrodes associated with the previously high-noise signals are now associated with low-noise signals. Although the multiplexers 412 are depicted as having two input ports, it should be understood that multiplexers might have any number of input ports as may be desirable.

In some examples, interface module 416 can include circuitry that may not entirely reject signals associated with high noise, but instead may sample (and transmit to controller 404) the signals associated with high noise at a different frequency (e.g., lower frequency) than the signals associated with low noise. In some examples, interface module 416 can include circuitry that may weigh the signals associated with high noise differently than the signals associated with low noise. For example, the high-noise signals can be given a lower weight (i.e., relative contribution to the overall ECG signal) than low-noise signals.

FIG. 4C depicts another variation of an interface module 426 that comprises amplifiers 420 and multiplexers 422, such that the signals from each measurement electrode 402 can be selected by the multiplexer before they are amplified. In still other variations, differential amplifiers may be used (in either the circuit topology of FIG. 4B or FIG. 4C), where the first input to a differential amplifier may be a measurement electrode, and the second input to the differential amplifier may be a reference electrode (and/or an electrode selected from a plurality of reference electrodes). In some examples, the input signals (e.g., from the plurality of measurement electrodes and a reference electrode or reference electrode array) to one or more differential amplifiers may be pre-selected by one or more multiplexers so that the low-noise ECG signals can be amplified and processed.

In some examples, the interface module 426 can be configured to group together (e.g., via one or more switches)

low-noise signals and can be configured to group together high-noise signals. The group of low-noise signals can be measured at one frequency, and the group of high-noise signals can be measured at another frequency. For example, the group of low-noise signals can be measured more frequently than the group of high-noise signals.

Figure 4D:
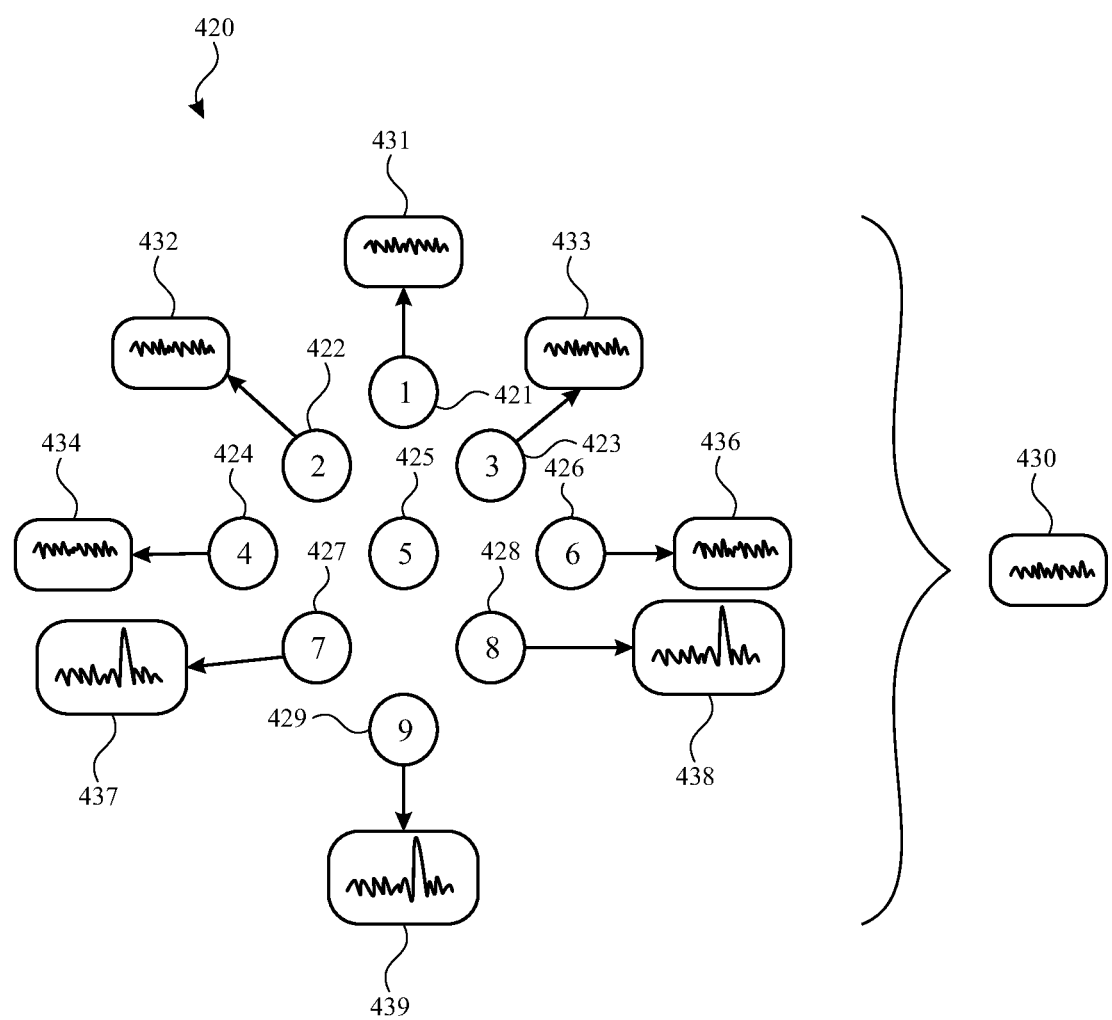
FIG. 4D depicts one example of the plurality of measurement electrodes and associated traces.

FIG. 4D depicts an exemplary plurality of measurement electrodes and associated spatial filtering of the measurement electrodes outputs. Plurality of measurement electrodes 420 comprises nine individually-addressable/controllable measurement electrodes 421-429 that can be arranged in a square (diamond) shape. In other examples, any number of measurement electrodes can be arranged in any shape. Each trace can be coupled to a unique electrode (e.g., electrode 421, 422, 423, 424, 426, 427, 428, 429, respectively (the trace coupled to electrode 425 is not depicted)), and separate signals 431, 432, 433, 434, 436, 437, 438, 439 can be measured and transmitted to the controller. Signals from the traces can be acquired during a portion of the cardiac cycle with minimal cardiac activity, such as the inter-beat interval. The controller can determine that the peak value or magnitude of the signals 437-430 from electrodes 427-429 can be higher than the peak value or magnitude of the signals from the other electrodes, and such fluctuations can be the result of noise.

In some examples, the controller can average all of the signals 431-439 to obtain an average signal that can represent a noise threshold against which the signals from the measurement electrodes can be compared. For example, the controller may compute the peak value or magnitude of that average signal, and compare the peak value or magnitude of each of the signals 431-439 with that of the average signal to identify measurement electrodes that have suprathreshold values or magnitudes. Such measurement electrodes can be considered as "high-noise" measurement electrodes. These high-noise electrodes may be determined to be located at or contacting skin regions that give rise to higher levels of noise, for example. For example, without wishing to be bound by theory, the noise that affects the electrodes 427-429 (which may be located in a contiguous spatial region) may arise from sweat glands that can be co-located with the electrodes 427-429. In some instances, the skin region that contacts electrodes 421-426 may have fewer, if any, sweat glands than the skin region contacted by electrodes 427-429. Once the controller has identified electrodes 427-429 as high-noise electrodes, the signals from the high-noise electrodes may be excluded from generating the overall ECG waveform. For example, electrodes 427-429 can be grouped together, and electrodes 421-426 can be grouped together. Signal 430 can represent the sum of the signals 431-436 associated with low-noise measurement electrodes; signals 437-439 from high-noise measurement electrodes can be excluded. The signals from electrodes 427-429 may be excluded by adjusting the channel selection of the multiplexer(s) in the interface module such that signals from high-noise measurement electrodes may not selected for transmission to the controller. In this manner, more bandwidth can be made available between the interface module and the control module for the transmission of signals from low-noise measurement electrodes 421-426. In some examples, the signals from high-noise measurement electrodes 427-429 may be transmitted to the controller (along with the signals from the low-noise measurements electrodes 421-426), but not included in the determination of the overall ECG waveform.

The device can operate with any configuration for sampling ECG data. For example, all measurement electrodes (e.g., measurement electrodes 421-429) can sample ECG data at the same time, and the signals can be transmitted to the controller at the same time. In some examples, the measurement electrodes can sample ECG data sequentially (e.g., electrode 421 can sample ECG data first, followed by electrode 422 sampling data second, etc.), and the signals can be transmitted to the controller sequentially. In some examples, the device can perform an initial scan including sampling all of the measurement electrodes to determine whether one or more measurement electrodes include suprathreshold noise levels. Subsequent scans can exclude the measurement electrodes with suprathreshold noise levels, but can include the electrodes with subthreshold noise levels.

In some examples, the device can simultaneously sample ECG data from multiple electrodes to further reject or disable electrodes. For example, electrode 421 and electrode 429 can simultaneously sample ECG data. If the noise levels from the measurements differ, then the device can determine whether to use the measurements from the measurement electrode with lower noise levels or disable the measurement electrode with higher noise levels.

Figure 4E:
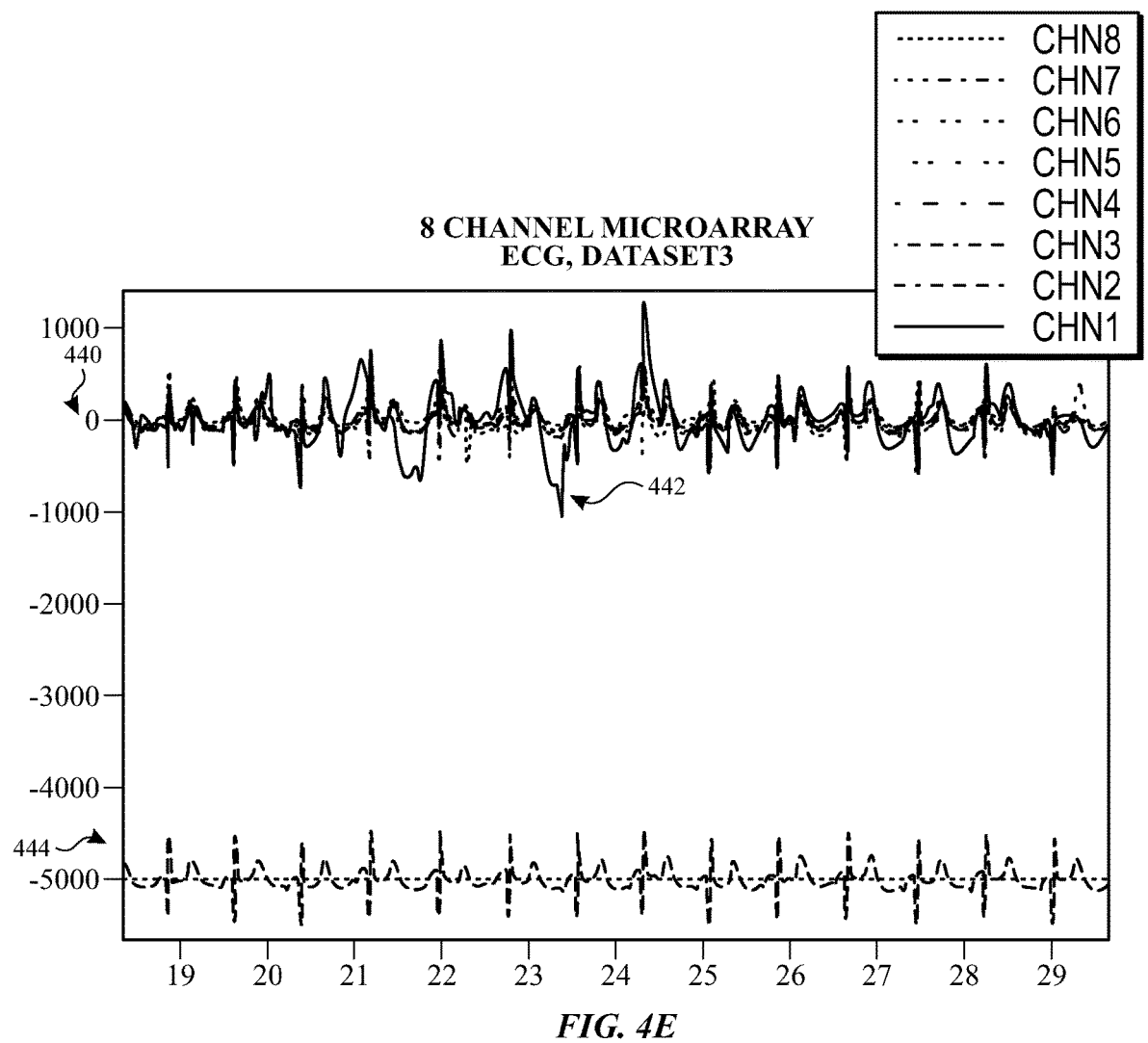
FIG. 4E illustrates example signals measured from eight measurement electrodes and an overall ECG waveform derived from the signals with subthreshold noise levels.

In some examples, each of the measurement electrodes can be coupled to a unique communication channel. FIG. 4E depicts an example of spatial filtering of ECG data from eight measurement electrodes (electrodes represented by channels 1-8). The signals 440 from the eight measurement electrodes can have varying degrees of noise, with the signal 442 from channel 8 having the greatest amount of noise. The signal 442 from channel 8 may be identified as having suprathreshold noise levels by the controller and can be filtered out (e.g., excluded from the computation of the overall ECG waveform). Signal 444 can be the overall ECG waveform generated by the data from channels 1-7, and can exclude data from channel 8. Spatial filtering the signals from the eight measurement electrodes to exclude data from channel 8 may help to preserve the integrity of the overall ECG waveform, and limit (or entirely eliminate) the effect of electrodes with suprathreshold noise levels on the ECG waveform.

Figure 5A:
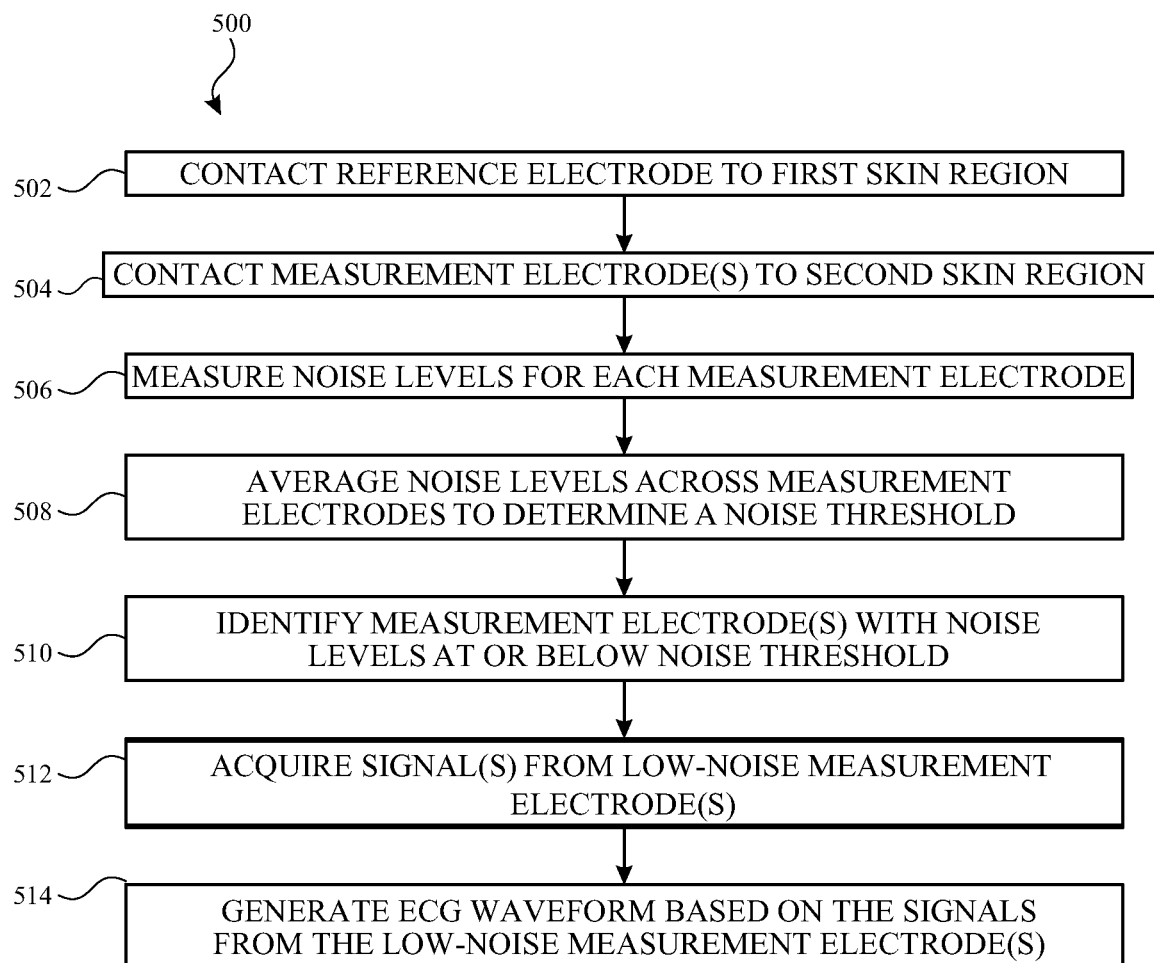
FIG. 5A is a flowchart that depicts a variation of a spatial filtering method.
Figure 5B:
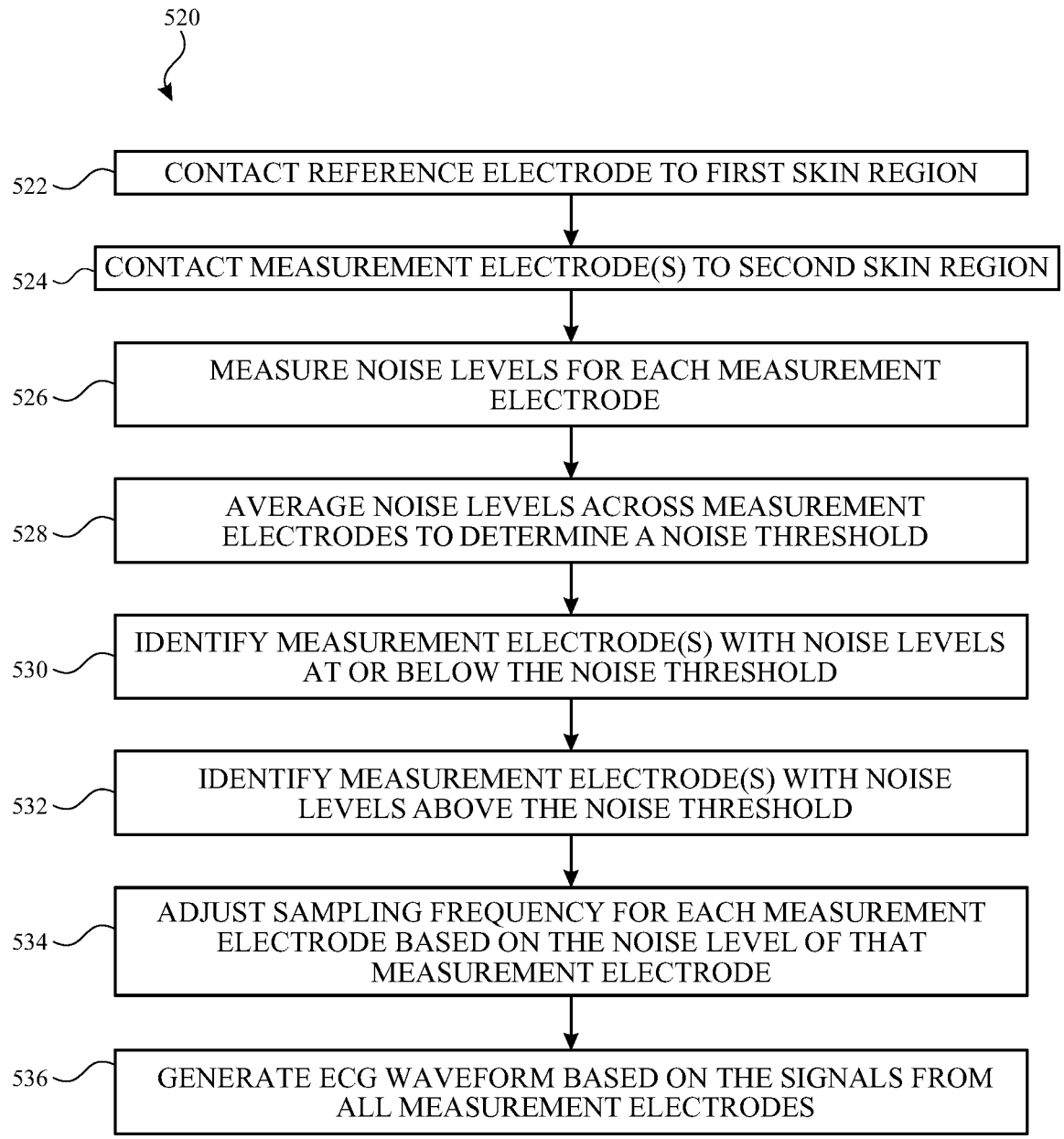
FIG. 5B is a flowchart that depicts a variation of a spatial filtering method.

FIGS. 5A-5B are flowchart depictions of variations of methods of spatial filtering that may be performed by a controller of a mobile or wearable device for acquiring ECG signals. Some methods of spatial filtering may completely eliminate or reject the signals from measurement electrodes that have noise levels that exceed the noise threshold. In some examples, signals from the measurements electrodes associated with noise levels that exceed the noise threshold can be included, but the signals can be scaled down (e.g., be associated with a lower weighting factor).

In some examples, the input from high-noise measurement electrodes can be completely eliminated or rejected, as depicted in FIG. 5A. Method 500 may comprise contacting a reference electrode to a first skin region in step 502, and contacting one or more of a plurality of measurement electrodes to a second skin region in step 504. For instances where the reference electrode can be located on a wrist-worn device such as a watch, method 500 may comprise putting on the watch such that the reference electrode can contact the skin region at or near the wrist, and the measurement electrode(s) can contact a second region of skin (e.g., a fingertip). For example, if the measurement electrode(s) are located on the watch, the user may touch the tip of his/her finger to the surface of the watch that has the measurement electrode(s).

In some examples, if the measurement electrode(s) are located on a separate accessory device, the user may contact the measurement electrode(s) by contacting the accessory device. After the reference electrode and the measurement electrode(s) have contacted the skin of the user, method 500 may comprise measuring the noise levels for each measurement electrode in step 506. For example, the impedance and/or electrical signals may be measured for each measurement electrode(s). Such measurements can be transmitted from the measurement electrode(s) to the interface module and then transmitted to the controller, using wired and/or unwired communications.

In some examples, the controller can optionally average the noise levels from each of the measurement electrode(s) in step 508. The average noise level can be used to determine a noise threshold against which the noise levels of each of the measurement electrodes can be compared. Alternatively, the noise threshold may be preselected or predetermined, and may be independent of the average measured noise level of the measurement electrodes. Alternatively, in some examples, a preselected or predetermined noise threshold may be adjusted based on the noise levels of the measurement electrodes (e.g., shifted upwards or downwards based on the computed average noise level). Once a noise threshold has been determined and/or calculated, the controller may identify the measurement electrodes with noise levels that are at or below the threshold noise levels (which may be referred to as "low-noise" measurement electrodes) in step 510. The controller may send a command signal to the interface module with instructions to acquire and transmit signals only from low-noise measurement electrode(s). Signals from high-noise measurement electrode(s) (i.e., any measurement electrodes that are not low-noise measurement electrodes) may be rejected by the interface module.

In some examples, the controller may send a command signal to the interface module to acquire and transmit signals from the measurement electrode(s) with the least amount of noise. For example, the controller may rank the measurement electrodes based on their relative noise levels and issue commands to the interface module to gather and transmit signals only from some (e.g., three, four, five, etc.), but not all, measurement electrodes with the least noise. After sufficient ECG data has been acquired by the controller (e.g., after a period of time, such as about 5-20 seconds), the controller may generate an ECG waveform based on the signals from the low-noise measurement electrodes in step 514. Optionally, the generated ECG waveform may be displayed to the user or practitioner and/or transmitted to a remote server for storage and/or further analysis.

In some examples, spatial filtering can include scaling down the signals associated with or under-sampling high-noise measurement electrode(s), as depicted in FIG. 5B. Method 520 may comprise contacting a reference electrode to a first skin region in step 522, and contacting a plurality of measurement electrodes to a second skin region in step 524. For examples where the reference electrode can be located on a wrist-worn device such as a watch, method 520 may comprise putting on the watch such that the reference electrode can contact the skin region at or near the wrist, and the plurality of measurement electrodes can contact a second region of skin (e.g., a fingertip). For example, if the plurality of measurement electrodes is located on the watch, the user may touch the tip of his/her finger to the surface of the watch that has the plurality of measurement electrodes.

In some examples, if the plurality of measurement electrodes is located on a separate accessory device, the user may contact the plurality of measurement electrodes by contacting the accessory device. After the reference electrode and the plurality of measurement electrodes contact to the skin of the user, method 520 may comprise measuring the noise levels for each measurement electrode in step 526. For example, the impedance and/or electrical signals may be measured for each measurement electrode. Such measurements can be transmitted from the measurement electrode(s) to the interface module and then transmitted to the controller, using wired and/or unwired communications.

In some examples, the controller can optionally average the noise levels from each of the measurement electrodes in step 528. The average noise level may be used as a noise threshold against which the noise levels of each of the measurement electrodes may be compared. Alternatively, the noise threshold may be preselected or predetermined and may be independent of the average measured noise level of the measurement electrodes. Alternatively, a preselected or predetermined noise threshold may be adjusted (e.g., shifted upwards or downwards based on the computed average noise level) based on the noise levels of the measurement electrodes. Once a noise threshold has been determined and/or calculated, the controller may identify the measurement electrode(s) (e.g., "low-noise" measurement electrodes) with noise levels that are at or below the noise threshold in step 530. The controller may also identify the electrodes (e.g., "high-noise" measurement electrodes) with noise levels that are above the noise threshold levels in step 532.

In some examples, the controller can send a command signal to the interface module with instructions to adjust the sampling frequency for low-noise and high-noise measurement electrodes in step 534. For example, the interface module can adjust the switching in the multiplexer(s) such that signals from low-noise measurement electrodes can be transmitted to the controller more frequently than signals from high-noise measurement electrodes. The sampling frequency of a particular measurement electrode can be inversely related (e.g., inversely proportional, etc.) to its noise level. For example, the noise levels of the plurality of measurement electrodes can be ranked by the controller; the frequency at which the multiplexer can switch to a particular measurement electrode and can transmit its signal to the controller can be inversely proportional to the ranking of that particular measurement electrode.

In some variations, the interface module can be configured to (e.g., using a plurality of staged multiplexers) provide a dedicated channel between low-noise measurements electrodes to the controller and then multiplex between the high-noise measurement electrodes. In some examples, the controller can prioritize the transmission of ECG data from low-noise measurement electrodes over high-noise measurement electrodes by increasing the multiplexer selection frequency and/or sampling frequency of the low-noise measurement electrodes. In some examples, the controller can reduce the selection frequency and/or sampling frequency of the high-noise measurement electrodes. In some instances, the controller can generate a good quality, low-noise ECG waveform, without increasing the power consumption or bandwidth requirements of the device.

Alternatively or additionally to adjusting the characteristics of data acquisition, the signal(s) from high-noise measurement electrode(s) can be processed differently by the controller as compared to the signals from the low-noise measurement electrode(s). For example, to the extent that the overall ECG waveform can be a weighted sum of the signals from the plurality of measurement electrodes, the controller may scale down the magnitude or weight of the signal from high-noise measurement electrodes when computing the overall ECG waveform. After sufficient ECG data has been acquired by the controller (e.g., after a period of time, such as about 5-20 seconds), the controller can generate an ECG waveform based on the signals from the low-noise measurement electrodes in step 522. Optionally, the generated ECG waveform may be displayed to the user or practitioner and/or transmitted to a remote server for storage and/or further analysis.

The variations of spatial filtering methods described above and depicted in FIGS. 5A-5B can classify the noise characteristics of the measurement electrodes before ECG data and/or signals are acquired and processed. In some examples, the noise characteristics of the measurement electrodes can be evaluated before, during, and/or after data acquisition. For example, in some instances where the user can move during data acquisition, a measurement electrode that was previously determined to have subthreshold noise levels may be affected by motion artifacts, acquiring signals with unfavorable noise characteristics. In such scenario, it may also be that a measurement electrode previously determined to have suprathreshold noise levels may have improved noise conditions, for example, due to better skin contact or being moved to a location with fewer sweat glands, etc. A controller that can evaluates the noise characteristics of the measurement electrodes throughout data acquisition interval may detect this change and may dynamically adjust the sampling frequency and/or grouping of the measurement electrodes, whose noise characteristics may have changed.

In some examples, where the overall ECG waveform can be a weighted sum of the signals from the measurement electrodes, the weighting factor may vary as a function of time such that when the signal levels from a particular measurement electrode exceed the noise threshold, the weighting factor can be dynamically changed (e.g., decrease for that time period). In some examples, when the signal levels from that same measurement electrode are below the noise threshold, the weighting factor can be dynamically changed (e.g., increased for that time period). The noise characteristics of the measurement electrodes may be performed on a sample-by-sample basis or at set time intervals during the ECG data acquisition period (e.g., for an acquisition period of 10 seconds, the noise characteristics of the measurement electrodes may be re-evaluated every second, or every two seconds, or every 0.5 seconds, etc.).

The controller can be configured to generate notifications to the user and/or medical practitioner regarding the signal quality and/or noise levels of the signals from the measurement electrodes. For example, if at any point the majority of the measurement electrodes have suprathreshold noise levels, and/or exceed a maximum acceptable noise threshold (i.e., such that an interpretable ECG waveform cannot be generated (e.g., the data is too sparse or the SNR is below a certain threshold)), the controller can prompt the user to re-position or otherwise adjust one or more measurement electrode(s). For example, the controller may suggest that the user position one or more measurement electrode(s) at a flatter anatomical region, and/or press one or more measurement electrode(s) to more intimately contact the skin surface, etc. In some examples, the controller can indicate exactly which measurement electrode(s) have unusual levels of noise, and the user may inspect those measurement electrode(s) and check their contact with the skin region. In some examples, the controller may also generate an ECG waveform form that may be projected to the user on a display of the mobile or wearable device, and/or transmitted to a remote server for storage and/or further analysis.

Although descriptions given herein have been in relation to certain examples, various additional examples and alterations to the described examples are contemplated within the scope of the disclosure. Thus, no part of the foregoing description should be interpreted to limit the scope of the disclosure as set forth in the following claims. For all of the examples described above, the steps of the methods need not be performed sequentially. The foregoing description, for purpose of explanation, has been described with reference to specific examples. However, the illustrative discussions above are not intended to be exhaustive or to limit the disclosure to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates examples in which users selectively block the use of, or access to, personal information data. The present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly describes use of personal information data to implement one or more various disclosed examples, the present disclosure also contemplates that the various examples can also be implemented without the need for accessing such personal information data. That is, the various examples of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

A device is disclosed. The device can comprise: one or more measurement electrodes configured to contact one or more first areas of a skin surface, each measurement electrode being independently measurable and configured to generate a measurement signal indicative of one or more electrical signals of a user, the measurement signal included in a plurality of measurement signals; and a controller configured to: receive the plurality of measurement signals, compare each measurement signal to a noise threshold, reject or apply a first weighting factor to each measurement signal having a level greater than or equal to the noise threshold, perform one or more of accepting and applying a second weighting factor to each measurement signal having a level less than the noise threshold, and determine one or more physiological parameters from the accepted measurement signals. Additionally or alternatively, in some examples, some of the one or more measurement electrodes are configured to contact an area of the skin surface different from other measurement electrodes. Additionally or alternatively, in some examples, the device further comprises: a reference electrode configured to contact a second area of the skin surface and located on a lower surface of a housing of the device, wherein the one or more measurement electrodes are located on an upper surface, opposite the lower surface, of the housing. Additionally or alternatively, in some examples, some of the one or more measurement electrodes are located at a first location of the device and others of the one or more measurement electrodes are located at a second location, separate and distinct from the first location, of the device. Additionally or alternatively, in some examples, the one or more first areas of the skin surface are located proximate to each other. Additionally or alternatively, in some examples, the device further comprises: one or more communications channels, each communication channel associated with one of the one or more measurement electrodes. Additionally or alternatively, in some examples, the one or more measurement electrodes include one or more first measurement electrodes and one or more second measurement electrodes, the one or more first measurement electrodes associated with a level of noise lower than the one or more second measurement electrodes, the device further comprising: one or more communications channels, each communication channel associated with one of the one or more first measurement electrodes; and one or more multiplexers configured to dynamically reconfigure connections of the one or more second measurement electrodes to the controller.

A method is disclosed. The method can comprise: contacting one or more first areas of a skin surface of a user with one or more measurement electrodes; for each measurement electrode, measuring one or more electrical signals of the user and generating one or more measurement signals indicative of the measured one or more electrical signals; transmitting the one or more measurement signals using one of one or more communications channels to a controller; and determining one or more physiological parameters from the transmitted one or more measurement signals. Additionally or alternatively, in some examples, the method further comprises: for each measurement electrode, comparing the one or more measurement signals to a noise threshold level; and determining one or more first measurement electrodes from the one or more measurement electrodes and one or more second measurement electrodes from the one or more measurement electrodes based on the comparison, the one or more first electrodes having measurement signals less than the noise threshold level and the one or more second electrodes having measurement signals greater than or equal to the noise threshold level or a standard deviation from the noise threshold level, wherein determining the one or more physiological parameters include measurement signals associated with the one or more first electrodes. Additionally or alternatively, in some examples, the determining the one or more physiological parameters excludes measurement signals associated with the one or more second electrodes. Additionally or alternatively, in some examples, the method further comprises: applying one or more first weighting factors to the measurement signals associated with the one or more first measurement electrodes; and applying one or more second weighting factors, less than the first weighting factor, to the measurement signals associated with the one or more second measurement electrodes. Additionally or alternatively, in some examples, each first weighting factor is inversely proportional to a noise level of the associated first measurement electrode, and each second weighting is inversely proportional to a noise level of the associated second measurement electrode. Additionally or alternatively, in some examples, after measuring the one or more electrical signals using each measurement electrode, for each first measurement electrode, measuring one or more electrical signals of the user and generating one or more second measurement signals indicative of the measured one or more electrical signals. Additionally or alternatively, in some examples, measuring the one or more electrical signals for each first measurement electrode includes a first measurement frequency, and measuring the one or more electrical signals for each second measurement electrode includes a second measurement frequency, the first measurement frequency greater than the second measurement frequency. Additionally or alternatively, in some examples, measuring the one or more electrical signals for each measurement electrode includes a frequency inversely proportional to a noise level associated with the measurement electrode. Additionally or alternatively, in some examples, the method further comprises: for each measurement electrode, measuring one or more second electrical signals of the user; generating one or more second measurement signals indicative of the measured one or more second electrical signals; comparing the one or more second measurement signals to the noise threshold level; determining a change in noise level based on the comparison; and reassigning the one or more measurement electrodes associated with the change in noise level. Additionally or alternatively, in some examples, the one or more first areas of the skin surface include a thumb and an index finger of the user, wherein the measuring the one or more electrical signals is after the thumb and index finger contact the one or more measurement electrodes. Additionally or alternatively, in some examples, the measuring the one or more electrical signals is simultaneous for all measurement electrodes, and the transmitting the one or more measurement signals is simultaneous. Additionally or alternatively, in some examples, the method further comprises: ordering noise levels associated with the one or more measurement electrodes; and determining one or more first measurement electrodes having a lower order than other measurement electrodes, wherein the determining the one or more physiological parameters include measurement signals associated with the one or more first measurement electrodes. Additionally or alternatively, in some examples, the method further comprises: comparing one or more measurement signals to a noise threshold level; and prompting the user to move at least one of the one or more measurement electrodes to a different area of the skin surface.

The invention claimed is:

1. A device comprising:
multiple measurement electrodes configured to contact multiple areas of a skin surface and to measure a plurality of signals, each measurement electrode being independently measurable and configured to measure a signal of the plurality of signals of a user; and
a controller configured to:
receive the plurality of signals,
compare each signal of the plurality of signals to a noise threshold derived from the plurality of signals from the multiple measurement electrodes,
reject or apply a first weighting factor to each signal having a level greater than or equal to the noise threshold,
perform one or more of accepting and applying a second weighting factor to each signal having a level less than the noise threshold, and
determine one or more physiological parameters from at least one or both of the accepted signals and the signals with the applied second weighting factor.

2. The device of claim 1, further comprising:
a reference electrode configured to contact a second area of the skin surface and located on a lower surface of a housing of the device, wherein the one multiple measurement electrodes are located on an upper surface, opposite the lower surface, of the housing.

3. The device of claim 1, wherein some of the multiple measurement electrodes are located at a first location on a housing and others of the multiple measurement electrodes are located at a second location on the housing, separate and distinct from the first location on the housing.

4. The device of claim 1, wherein the multiple measurement electrodes are located proximate to each other.

5. The device of claim 1, further comprising:
one or more communications channels, each communication channel associated with one of the multiple measurement electrodes.

6. The device of claim 1, wherein the multiple measurement electrodes include one or more first measurement electrodes and one or more second measurement electrodes, the one or more first measurement electrodes associated with a level of noise lower than the one or more second measurement electrodes, the device further comprising:
one or more communications channels, each communication channel associated with one of the one or more first measurement electrodes; and
one or more multiplexers configured to dynamically reconfigure connections of the one or more second measurement electrodes to the controller.

7. A device, comprising:
multiple measurement electrodes configured to contact multiple areas of a skin surface and measure a plurality of measurement signals, each measurement electrode being independently measurable and configured to measure a signal of the plurality of measurement signals of a user; and
a controller configured to:
receive the plurality of measurement signals,
compare each signal of the plurality of measurement signals to a noise threshold derived from the plurality of measurement signals of the multiple measurement electrodes,
perform one or more of accepting or applying a second weighting factor to each signal of the plurality of measurement signals having a level less than the noise threshold, and
determine one or more physiological parameters from at least one or both of the accepted signals and the signals with the applied first weighting factor.

8. The device of claim 1, wherein the controller is further configured to reject or apply a second weighting factor to each signal having a level greater than or equal to the noise threshold.

9. The device of claim 1, further comprising:
a communication channel configured to transmit the plurality of signals to the controller.

10. The device of claim 9, wherein at least one signal of the transmitted plurality of signals is a differential signal.

11. The device of claim 9, wherein the communication channel transmits the plurality of signals to the controller wirelessly.

12. The device of claim 1, further comprising:
a multiplexer configured to:
spatially filter the plurality of signals based on a command from the controller and,
selective transmitting a subset of the plurality of signals based on the command from the controller.

13. A method comprising:
contacting multiple areas of a skin surface of a user with multiple measurement electrodes;
measuring a plurality of electrical signals from the user with the multiple measurement electrodes;
generating a plurality measurement signals indicative of the measured plurality of electrical signals;
transmitting the plurality of measurement signals using wireless communication channels to a controller,
the controller configured to:
receive the plurality of measurement signals,
compare each of the plurality of measurement signals to a noise threshold that is derived from the plurality of measurement signals from the multiple measurement electrodes;

reject or apply a first weighting factor to each of the plurality of measurement signals having a level greater than or equal to the noise threshold, perform one or more of accepting and applying a second weighting factor to each of the plurality of measurement signals having a level less than the noise threshold; and determining one or more physiological parameters from the at least one or both of the accepted signals and the signals less than the noise threshold.

14. The method of claim 13, further comprising:

categorizing at least one first measurement electrodes and at least one second measurement electrodes from the multiple measurement electrodes based on the comparison, the at least one first measurement electrodes having measurement signals less than the noise threshold level and the at least one second measurement electrodes having measurement signals greater than or equal to the noise threshold level or a standard deviation from the noise threshold level, wherein determining the one or more physiological parameters include the measurement signals associated with the at least one first measurement electrodes.

15. The method of claim 14, further comprising:

applying one or more first weighting factors to the measurement signals associated with the at least one first measurement electrodes; and applying one or more second weighting factors, less than the first weighting factor, to the measurement signals associated with the at least one second measurement electrodes.

16. The method of claim 15, wherein each first weighting factor of the one or more first weighting factors is inversely proportional to a noise level of the associated at least one first measurement electrodes, and each second weighting factor of the one or more second weighting factors is inversely proportional to a noise level of the associated at least one second measurement electrodes.

17. The method of claim 14, wherein measuring the electrical signals for the at least one first measurement electrodes includes a first measurement frequency, and measuring the electrical signals for the at least one second measurement electrodes includes a second measurement frequency, the first measurement frequency greater than the second measurement frequency.

18. The method of claim 13, further comprising:

ordering noise levels associated with the multiple measurement electrodes; and determining one or more first measurement electrodes having a lower order than other measurement electrodes, wherein the determining the one or more physiological parameters include measurement signals associated with the one or more first measurement electrodes.

19. The method of claim 13, further comprising:

prompting the user to move at least one of the multiple measurement electrodes to a different area of the skin surface.

* * * * *